(12) United States Patent
Sutoris et al.

(10) Patent No.: US 6,350,827 B1
(45) Date of Patent: Feb. 26, 2002

(54) PRESSURIZATION OF ETHYLENICALLY UNSATURATED MONOMERS

(75) Inventors: Heinz Friedrich Sutoris, Frankenthal; Andreas Deckers, Flomborn; Wilhelm Weber, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/452,451

(22) Filed: Dec. 2, 1999

(30) Foreign Application Priority Data

Dec. 22, 1998 (DE) .......................................... 198 59 391

(51) Int. Cl.$^7$ .............................. C08F 2/40; C07F 7/02
(52) U.S. Cl. .................. 526/83; 526/204; 526/318.6; 546/14
(58) Field of Search .............. 526/83, 204, 318.6; 546/14

(56) References Cited

U.S. PATENT DOCUMENTS 5,290,888 A    3/1994    Gatechair et al.
5,872,252 A *   2/1999    Sutoris et al. .......... 526/204 X

FOREIGN PATENT DOCUMENTS

| EP | 0 811 590 | 12/1997 |
| EP | 0 911 733 | 4/2000 |
| WO | WO 98/58038 | 12/1998 |

* cited by examiner

Primary Examiner—Fred Teskin
(74) Attorney, Agent, or Firm—Oblon, Spivak, McClelland, Maier & Neustadt, P.C.

(57) ABSTRACT

Disclosed is a process for pressurizing ethylenically unsaturated monomers to 200–5000 bar in the absence of a polymerization initiator, which comprises effecting said pressurizing in the presence of nitroxyl compounds of the formula I

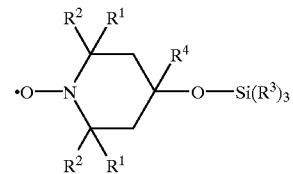

where $R^1$ and $R^2$ are singly $C_1$–$C_4$-alkyl or combine with the joining carbon atom to form a 5- or 6-membered saturated hydrocarbon ring, $R^3$ is $C_1$–$C_4$-alkyl, and $R^4$ is hydrogen or $C_1$–$C_{12}$-alkyl.

Also disclosed are a process for preparing copolymers by such pressurization and subsequent polymerization and copolymers obtainable thereby.

7 Claims, No Drawings

PRESSURIZATION OF ETHYLENICALLY UNSATURATED MONOMERS

The present invention relates to a process for pressurizing ethylenically unsaturated monomers to 200–5000 bar in the absence of a polymerization initiator, which comprises effecting said pressurizing in the presence of nitroxyl compounds of the formula I

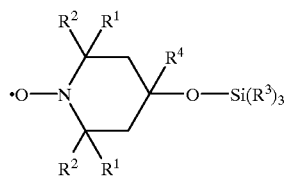

where
- $R^1$ and $R^2$ are singly $C_1$–$C_4$-alkyl or combine with the joining carbon atom to form a 5- or 6-membered saturated hydrocarbon ring,
- $R^3$ is $C_1$–$C_4$-alkyl, and
- $R^4$ is hydrogen or $C_1$–$C_{12}$-alkyl.

The present invention further relates to a process for preparing copolymers by such pressurization and subsequent polymerization and to copolymers obtainable thereby.

Derivatives of sterically hindered amines have long been known for use as stabilizers of plastics and of free-radically polymerizable monomers.

EP-A-178 168 discloses a method of inhibiting α,β-ethylenically unsaturated monocarboxylic acids, for example acrylic acid, in the course of their distillative workup.

U.S. Pat. No. 5 449 724 describes a process for preparing thermoplastic ethylene homopplymers and copolymers at 40–5000° C. and 500–5000 bar in the presence of a free-radical initiator and a stable free radical compound. The presence here of the stable free radical compound, especially of derivatives of 2,2,6,6-tetramethylpiperidine-N-oxyl, leads to a particularly narrow molecular weight distribution and, associated therewith, to special physical properties on the part of the polymers.

EP 0 811 590 describes a process for pressurizing ethylenically unsaturated monomers to 500–5000 bar in the presence of polymerization inhibitors. Those mentioned include nitroxyl compounds.

Examples 1 to 3 of EP 0 811 590 demonstrate the advantageous effect of various amounts of N,N'-bis(2,2,6,6-tetramethyl-piperidin-1-oxyl-4-yl)-N,N'-bisformylhexamethylenediamine with regard to the inhibition of the premature polymerization of an ethylene/acrylic acid mixture.

For instance, the presence of the inhibitor mentioned enables the second compressor to run for not less than 124 h compared with only 27 h in the absence of the inhibitor. The longer running times are possible because of the distinctly reduced formation of polymer, since the latter leads to deposits and hence to leaks in the second compressor and makes it necessary to switch off and clean the second compressor.

The pressurization of ethylenically unsaturated monomers to 500–5000 bar, especially the pressurization of monomer mixtures comprising ethylene and acrylic acid or acrylic acid derivatives, is generally observed to be accompanied— frequently even prior to the desired polymerization—by instances of unwanted, premature polymerization in the compressors and precompressors, leading to the formation of deposits and making it necessary to clean the compressors on a regular basis at short intervals.

Customary inhibitors, such as methylhydroquinone and hydroquinone, provide only minimal inhibition and have to be added in high concentrations. Nitroxyl compounds as known from EP 0 811 590 provide a distinctly better effect, but there is still a permanent need for even more effective inhibitors.

It is an object of the present invention to provide a process for pressurizing ethylenically unsaturated monomers which is even more effective than existing processes at reducing deposit formation due to premature polymerization during pressurization.

We have found that this object is achieved by a process for pressurizing ethylenically unsaturated monomers to 200–5000 bar in the absence of a polymerization initiator, which comprises effecting said pressurizing in the presence of nitroxyl compounds of the formula I shown at the beginning.

All customary ethylenically unsaturated monomers are pressurizable by the process of the invention. Examples of suitable monomers are ethylene, propylene, butene and butadiene and also vinyl esters of $C_2$–$C_{18}$-alkanecarboxylic acids such as vinyl acetate and vinyl propionate, $C_2$–$C_{18}$-alkyl esters of acrylic and methacrylic acid such as methyl, ethyl, propyl, butyl and 2-ethylhexyl acrylate and methacrylate, esters of monoethylenically unsaturated dicarboxylic acids such as mono-and diesters of maleic and fumaric acid, monoethylenically unsaturated carboxylic acids such as acrylic acid, methacrylic acid, maleic acid and fumaric acid, amides of monoethylenically unsaturated carboxylic acids such as acrylamide, methacrylamide, N-mono($C_1$–$C_{18}$)alkylacrylamide, N-mono($C_1$–$C_{18}$)alkylmethacrylamide, N-di($C_1$–$C_{18}$)alkylacrylamide and N-di($C_1$–$C_{18}$)alkylmethacrylamide, monoethylenically unsaturated alcohols, $C_1$–$C_4$-alkyl vinyl ethers and N-vinyl heterocyclic compounds such as N-vinylpyrrolidone, N-vinylcaprolactam and N-vinylimidazoles and also N-vinylformamide.

Suitable monomer mixtures include in particular those comprising ethylene, propylene, butene and/or butadiene and optionally one or more of the comonomers mentioned above. The process of the invention is particularly useful for pressurizing monomer mixtures used for copolymerization.

More particularly, suitable monomers/comonomers also include acrylic acid and/or methacrylic acid and/or derivatives thereof.

Examples of suitable derivatives of these acids are the $C_1$–$C_{18}$-alkyl esters, $C_1$–$C_{18}$-mono- and dialkylamides and also the unsubstituted amides. Examples of useful $C_1$–$C_{18}$-alkyl groups are methyl, ethyl, n-propyl, isopropyl, n-butyl, isobutyl, sec-butyl, tert-butyl, n-pentyl, isopentyl, sec-pentyl, tert-pentyl, neopentyl and also the various isomeric hexyl, heptyl, octyl, nonyl, decyl, undecyl, dodecyl, tridecyl, tetradecyl, pentadecyl, hexadecyl, heptadecyl and octadecyl radicals.

The process of the invention is particularly useful for pressurizing mixtures of ethylene and acrylic acid or methacrylic acid.

Examples of possible $C_1$–$C_4$-alkyl for $R^1$, $R^2$ and $R^3$ in formula I include methyl, ethyl, n-propyl, i-propyl, n-butyl, i-butyl, sec-butyl or tert-butyl.

$R^1$ and $R^2$ each preferably represent the same $C_1$–$C_4$-alkyl. Particularly preferably, $R^1$ and $R^2$ are both methyl.

$R^1$ and $R^2$ may also combine with the joining carbon atom to form a 5- or 6-membered saturated hydrocarbon ring. For instance, $R^1$ and $R^2$ together may be a tetra- or pentamethylene group.

The $R^3$ radicals can be different, but they are preferably each the same $C_1$–$C_4$-alkyl. Preferably, every $R^3$ is tert-butyl or every $R^3$ is i-propyl, particularly preferably methyl.

$C_1$–$C_{12}$-alkyl $R^4$ includes for example the abovementioned $C_1$–$C_4$-alkyl groups and also pentyl, sec-pentyl, tert-pentyl, neopentyl, hexyl, 2-methylpentyl, heptyl, 2-methylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl and isododecyl (the designations isooctyl, isononyl and isodecyl are trivial names derived from the carbonyl compounds obtained by the oxo process; cf. Ullmann's Encyclopedia of Industrial Chemistry, 5th Edition, Vol. Al. pages 290–293, and also Vol. A10, pages 284 and 285).

In addition to the nitroxyl compounds of the formula I, the process of the invention may also utilize costabilizers. Examples of suitable costabilizers are aromatic nitro or nitroso compounds and also hydroxylamines.

Examples of useful aromatic nitro compounds are 1,3-dinitrobenzene, 1,4-dinitrobenzene, 2,6-dinitro-4-methylphenol, 2-nitro-4-methylphenol, 2,4,6-trinitrophenol, 2,4-dinitro-1-naphthol, 2,4-dinitro-6-methylphenol, 2,4-dinitrochlorobenzene, 2,4-dinitrophenol, 2,4-dinitro-6-sec-butylphenol, 4-cyano-2-nitrophenol, 3-iodo-4-cyano-5-nitrophenol, particularly preferably 2,6-dinitro-4-methylphenol, 2-nitro-4-methylphenol, 2,4-dinitro-6-sec-butylphenol or 2,4-dinitro-6-methylphenol.

Examples of useful aromatic nitroso compounds include p-nitrosophenol, p-nitroso-o-cresol and p-nitroso-N,N'-diethylaniline.

Useful costabilizers further include compounds selected from the group consisting of the quinones, the phenothiazines and the phenols, alone or combined with the aforementioned aromatic nitro or nitroso compounds and also hydroxylamines.

Examples of suitable substituted phenols are 4-tert-butylpyrocatechol, methoxyhydroquinone, 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris (3,5-di-tert-butyl-4-hydroxybenzyl)-benzene, 1,3,5-tris(3,5-di-tert-butyl-4-hydroxybenzyl) isocyanurate, 1,3,5-tris[β-(3,5-di-tert-butyl-4-hydroxyphenyl) propionyloxy-ethyl] isocyanurate, 1,3,5-tris(2,6-dimethyl-3-hydroxy-4-tert-butylbenzyl) isocyanurate and pentaerythritol tetrakis[β-(3,5-di-tert-butyl-4-hydroxyphenyl)propionate].

The nitroxyl compounds of the formula I are used in the pressurization process of the invention in a concentration in the range from 0.00001 to 1% by weight, based on the amount of monomers to be pressurized, preferably in the range from 0.0001 to 0.1% by weight. This concentration range also holds for the costabilizers mentioned.

The process of the invention pressurizes the monomers to a pressure in the range from 200 to 5000 bar. Pressurization is preferably carried out stepwise, and the final pressure is preferably in the range from 1000 to 4000 bar, particularly preferably in the range from 1500 to 3000 bar.

Pressurization temperatures are preferably in the range from 20 to 1400° C., particularly preferably in the range from 30 to 100° C.

The pressurization process of the invention does not utilize a polymerization initiator. For the purposes of the present invention, the term "polymerization initiator" covers all compounds which are added to the monomers to initiate the free-radical polymerization, such as azo compounds, organic peroxides and hydroperoxides. Any oxygen present in the mixture to be pressurized shall not be considered a polymerization initiator.

The pressurization process of the invention is preferably part of a high-pressure copolymerization process which comprises employing a process of the invention to pressurize the comonomers individually or mixed and then polymerizing at from 50 to 350° C. by adding a polymerization initiator.

The preferred polymerization temperature is in the range from 150 to 300° C., and the preferred pressure is in the range from 1000 to 4000 bar, particularly preferably in the range from 1500 to 3000 bar.

The polymerization can be carried out according to customary methods, for example in tubular reactors or in autoclave reactors. Any customary additives—molecular weight regulators, solvents, etc., for example—can be present in the polymerization mixture.

The advantage of this novel polymerization process resides not just in the longer running times of the compression apparatus, but also in an improvement in the products of the polymerization. For instance, when ethylene and acrylic acid are to be copolymerized, the acrylic acid in particular has a tendency to undergo premature polymerization in the course of pressurization. This leads to copolymer comprising fractions of acrylic acid homopolymer or at least containing homopolymer regions and hence to compromised product homogeneity and process reproducibility. The copolymers obtainable by the process of the invention, in contrast, are substantially homogeneous.

EXAMPLES 1–3

The experimental procedure was similar to that of examples 1 to 3 of EP 0 811 590 except that the compound N,N'-bis(2,2,6,6-tetramethylpiperidin-l-oxyl-4-yl)-N,N'-bis-formylhexamethylenediamine was replaced by 1-oxyl-4-trimethylsiloxy-2,2,6,6-tetramethylpiperidine ("TMS-TEMPO").

A precompressor was used to compress ethylene to a pressure of 220 bar. The compressed gas stream (1400 kg/hour) was admixed over 60 minutes with 85 1 of a 1/1 (v/v) acrylic acid and isododecane mix in which the amounts of TMS-TEMPO reported in the table had been dissolved. The mixture was pressurized to 2300 bar in a second compressor and continuously transferred into a 35 1 flowthrough steel autoclave. The polymerization was initiated with 0.0025 mol % (based on the total molar amount of monomers) of tert-butyl perpivalate. The reaction temperature was 220° C. The reaction was terminated as soon as the second compressor's gas leak rate due to deposits exceeded 50 kg/hour.

The table which follows shows the results of the experiments (the bracketed data relate to the inhibitor used in EP 0 811 590):

| Example | Inhibitor conc. [% by wt.] | Running time [h] |
| --- | --- | --- |
| 1 | 0.020 | >168 (>168) |
| 2 | 0.010 | >168 (>168) |
| 3 | 0.005 | >168 (124) |
| Comparative | 0 | 25 (27) |

The use of TMS-TEMPO provides running times of more than one week for concentrations as low as 0.005% by weight. In contrast, the conventional inhibitor has to be added in up to twice this concentration to produce the same effect.

We claim:

1. A process for pressurizing ethylenically unsaturated monomers to 200–5000 bar in the absence of a polymerization initiator, which comprises effecting said pressurizing in the presence of nitroxyl compounds of the formula I

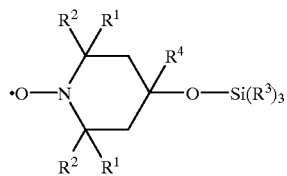

where $R^1$ and $R^2$ are singly $C_1$–$C_4$-alkyl or combine with the joining carbon atom to form a 5- or 6-membered saturated hydrocarbon ring, $R^3$ is $C_1$–$C_4$-alkyl, and $R^4$ is hydrogen or $C_1$–$C_{12}$-alkyl.

2. A process as claimed in claim 1, wherein said ethylenically unsaturated monomers are mixtures comprising ethylene, propylene, butene and/or butadiene.

3. A process as claimed in claim 1, wherein said ethylenically unsaturated monomers are mixtures comprising acrylic acid and/or methacrylic acid and/or derivatives thereof.

4. A process as claimed in claim 1, wherein said ethylenically unsaturated monomers are mixtures comprising ethylene and acrylic acid or methacrylic acid.

5. A process as claimed in claim 1, wherein said pressurizing is effected in the presence of hydroxylamines or of aromatic nitro or nitroso compounds.

6. A process as claimed in claim 1, wherein said pressurizing is effected in the presence of a compound selected from the group consisting of the quinones, the phenothiazines and the phenols.

7. A process for preparing copolymers, which comprises employing a process as claimed in claim 1 to pressurize the comonomers individually or mixed and then polymerizing at from 50 to 350° C. by adding a polymerization initiator.

* * * * *